US007459418B1

(12) United States Patent
Ozment

(10) Patent No.: US 7,459,418 B1
(45) Date of Patent: Dec. 2, 2008

(54) REPLENISHABLE SOAP BAR

(76) Inventor: Alden Ozment, 116 Hunter Creek Dr., Longview, TX (US) 75605

( * ) Notice: Subject to any disclaimer, the term of this patent is extended or adjusted under 35 U.S.C. 154(b) by 0 days.

(21) Appl. No.: 11/851,868

(22) Filed: Sep. 7, 2007

Related U.S. Application Data

(63) Continuation of application No. 10/901,890, filed on Jul. 29, 2004, now abandoned.

(51) Int. Cl.
*A61K 7/50* (2006.01)

(52) U.S. Cl. ....................... 510/141; 510/142; 510/143; 510/144; 510/152

(58) Field of Classification Search ....................... None
See application file for complete search history.

(56) References Cited

U.S. PATENT DOCUMENTS 4,277,358 A * 7/1981 Hopkins ..................... 510/143
4,308,157 A * 12/1981 Di Giovanna ............... 425/438
4,438,010 A * 3/1984 Lindauer et al. ............ 510/143
5,221,506 A * 6/1993 Dulin ......................... 510/120

* cited by examiner

*Primary Examiner*—Necholus Ogden, Jr.
(74) *Attorney, Agent, or Firm*—Stites & Harbison, PLLC; David W. Nagle, Jr.; Robert C. Yang

(57) ABSTRACT

A reusable minimal use soap bar comprising a structural core surrounded by a soap layer composition existing in a solid phase. The soap bar can be single or multiple use, depending on the thickness of the soap layer around the core. After use the structural core is replenished with a fresh coating of soap. A method for stripping any existing soap layer and replenishing the core with a fresh coating of soap for reuse is disclosed.

12 Claims, 3 Drawing Sheets

REPLENISHABLE SOAP BAR

RELATED APPLICATIONS

This application is a continuation of Ser. No. 10/901,890 filed Jul. 29, 2004, now abandoned.

FIELD OF THE INVENTION

This application relates to soap in bar form, and more particularly to an improved single use soap bar having a structural core which is coated with a soap layer that after use can be stripped and replenished with a fresh soap layer for reuse. This application also provides a method for stripping the existing soap layer and replenishing the structural core with a fresh soap layer.

BACKGROUND OF THE INVENTION

The need for conventional bar soap is common in today's hospitality industry. Most hotels provide each guest room with one or more bars of soap, including hand and bath soaps. Guests tend to stay for short periods of time and do not use the entire bar of provided soap during their stay. Conventionally new bars of soap are placed in the guest rooms each day and the used bars of soap are disposed of. As a result, much of the soap supplied in the hotel rooms is wasted adding to the cost of operating the hotel. To reduce this soap bar waste, the hospitality industry has made hotel soap bars smaller in dimension. However, the smaller bar does not completely eliminate waste many people prefer the larger dimensioned soap bar for ease of use.

Several U.S. patents describe soap bars with structural cores to reduce wastage. For example, U.S. Pat. No. 5,221,506 issued to Dulin (1993) describes a soap bar having a soap-impregnated sponge core. The sponge core of the '506 patent is preferably open celled and impregnated with soap and is exposed as the outer layers of the original soap bar are worn from use. Once the soap is washed away from the original soap bar and the sponge, the user is left with a usable sponge. In the '506 patent waste is reduced by the soap layers leading directly to and within a sponge and as the soap layers are worn away the sponge supports the sliver of remaining soap so that it can continue to be used and thus eliminates wasting the sliver of soap.

U.S. Pat. No. 4,438,010 issued to Lindauer et al. (1984) discloses a bar of soap with a perfumed plastic core" in contact with the soap substance and method for making the same. Similar to the '506 patent, the perfumed core of the '010 patent is exposed as the outer layers of the original soap bar are worn from use and waste is reduced by the soap layers leading directly to the perfumed core.

However, in the embodiments described in the patents, the core is disposed of as waste along with the unused soap, thereby actually increasing the cost of utilizing cored bar soap. The foregoing patents are not concerned with reusing the structural core with a fresh layer of soap. Rather, they are targeted at reducing soap waste as the bar is worn down to a sliver from repeated use. Currently there are no known soap bars comprising a soap layered structural core, which can be repeatedly recharged for use. More recently it has become common practice to provide the guest with liquid or gelled body soap in a container that can be hygienically used by different individuals. However, liquid soaps can be cost prohibitive and many users prefer solid bars of soap to the liquid body wash.

For the hospitality industry, soap bars are replaced daily or at least with each new guest. Normally the soap bars are only minimally used and a substantial amount of useable soap is wasted.

It is therefore a paramount object of the present invention to provide a soap bar designed for minimal use.

It is another object of the invention to provide a minimal use soap bar having a structural core which is coated with soap and can be repeatedly cleaned and replenished with a fresh soap layer for hygienic reuse.

It is an additional object of the present invention to provide a hygienic soap bar, having minimized capacity for contamination with harmful germs and that can be used by different individuals without wasting soap.

These and other objects and advantages of the present invention will become apparent upon a review of the following description.

SUMMARY OF THE INVENTION

The present invention is an improved bar of soap designed for minimal use and to a method of making the same. The hygienically reusable soap bar of the present invention comprises a structural core, over one or more surfaces of which is deposited a layer of soap. The used soap bar is collected on a regular basis for stripping of the coating of soap recoating with a fresh coat of soap for reuse so that the user is using a fresh bar of soap. Specifically, this includes a soap bar having a reusable structural core over which lies a soap layer that is replenished to provide the fresh bar of soap that can be hygienically used by another person without the wastage of soap that occurs when the soap is changed on a daily or frequent interval. This invention provides a meaningful solution to the issue of soap waste. The soap bar and structural core can be in any geometric configuration.

The method of the present invention is disclosed for recharging the reusable core that includes the steps of placing a reusable structural core inside a pool of liquefied soap composition into the cavity and hardening the soap composition to form a soap layer around the structural core.

DESCRIPTION OF THE DRAWINGS

A more thorough understanding of the operation and advantages of the present invention can be had by referring to the following detailed description which refers to the following figures.

DETAILED DESCRIPTION OF THE INVENTION

As used herein the terms "replenishable", "rechargeable" and "recharging" are used synominously to mean the application of or the ability to apply a fresh layer of soap over one or more surfaces of substrate. The term "core" or "reusable core" refers to the substrate over which a layer of soap is applied. The term "minimal use" refers to a bar of soap designed for short term use, such as one or two days, as would be the case in a hotel or the like where the soap in guest rooms is replaced for each new guest, normally on a daily basis.

The present invention is an improved minimal use bar of soap and method of making the same. More particularly, the present invention relates to a reusable soap bar having a structural core with a rechargeable soap layer. As will become clearer in the description that follows, the reusable and rechargeable soap bar of the present invention provides a meaningful solution to the issue of soap waste.

Figure 1:
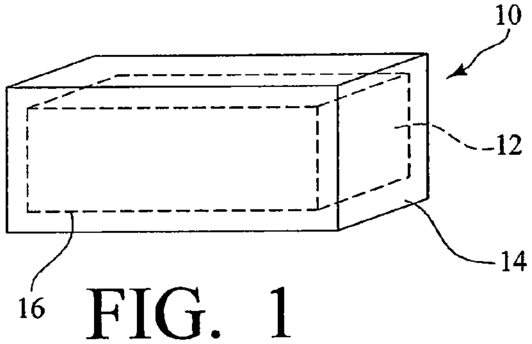
FIG. 1 is a perspective view of a rectangular shaped soap bar of the present invention containing a rectangular shaped core.
Figure 2:
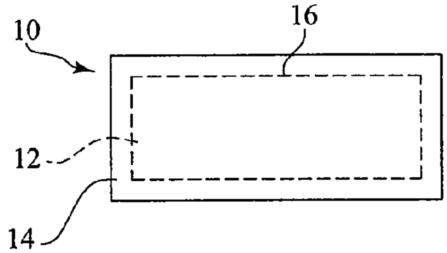
FIG. 2 is a front view of the soap bar in FIG. 1.
Figure 3:
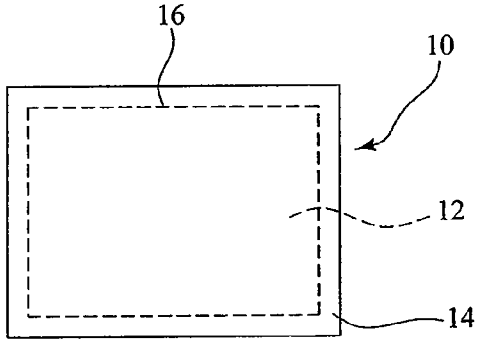
FIG. 3 is a top view of the soap bar of FIG. 1.
Figure 4:
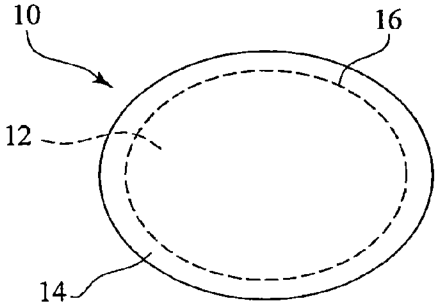
FIG. 4 is a perspective view of a shaped soap bar of the present invention defining an ellipsoid surface and containing an ellipses shaped core.

Referring now to FIGS. 1-3, there is illustrated one embodiment of the present invention comprising a soap bar 10 containing a structural core 12, which structural core 12 can be recharged with a soap layer 14 and reused repeatedly. FIGS. 1-3 show the soap bar of the present invention, shown generally as 10, in a rectangular configuration, defining front, rear, top and side faces. However, it is conceived that the soap bar 10 could be any geometric configuration, including traditional and novelty shapes. For example, FIG. 4 illustrates an embodiment of the invention in which the soap bar 10 has an elliptical configuration.

The soap bar core 12 may be any material inert with respect to soap and water and which is capable of withstanding the temperatures and pressures applied during the stripping and replenishing process. For example, a polymeric material such as polyethylene, polyvinyl, polyurethane, polyolefin, and combinations thereof, can be used with good results. It is preferred that the core 12 comprise 25% to 90% of the volume of the finished soap bar 10. In one embodiment, the surface 16 of the core 12 can be roughened or otherwise textured to aid in adherence of the soap layer 14 on the core 12. The core 12 must be able to maintain its stable form despite the temperature of the liquid soap used in making the soap layer 14.

The soap layer 14 surrounding the core 12 can be any soap composition which is in a solid phase at room temperature, including but not limited to, hand soap, bath soap, transparent and nontransparent soap, glycerin soap and perfumed soap. It is conceived that the soap layer 14 be designed for minimal use before replenishment of the core 12 with a fresh layer of soap. This may include only a single use of the soap bar 10 or may include several uses before replenishment, depending on the thickness of the soap layer 14 over the core 12. After the soap bar 10 has been used, the soap layer 14 is removed from the core 12 by a stripping process prior to recoating the core 12 with a fresh layer of soap. The stripping process entails wetting the bar 10 with a fluid, such as water, having a temperature and/or pressure sufficient to melt or solubilize the soap layer 14 resulting in a clean and exposed core 12. For example, the stripping process can be a carried out by apparatus in which the used soap bars 10 are contacted by jets of hot water to liquify and wash away the soap layer 14 from the core 12. A water temperature of between about 115° F. and 140° F. is suitable for stripping the used soap layer 14 from the core 12. Other fluids that could be used in the stripping process include hot air or any organic liquid having a temperature and/or pressure sufficient to melt or solubilize the soap layer 14. Although other fluids can be used in the stripping process, for the purposes of discussion, the description will focus on the use of hot water.

Figure 7:
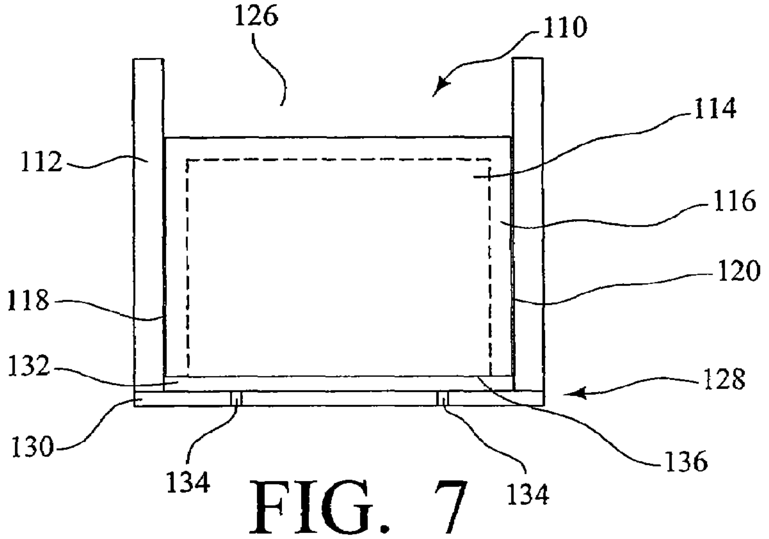
FIG. 7 is a cross-sectional view of a soap bar of the present invention in a mold for stripping and recharging in a closed position.
Figure 8:
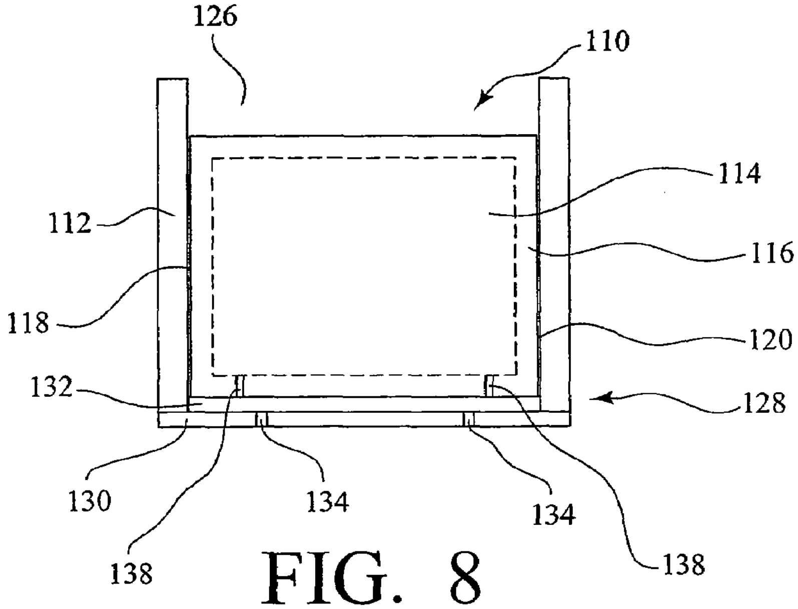
FIG. 8 is a cross-sectional view of a soap bar of the present invention in a mold having risers for the soap bar to rest upon.
Figure 9:
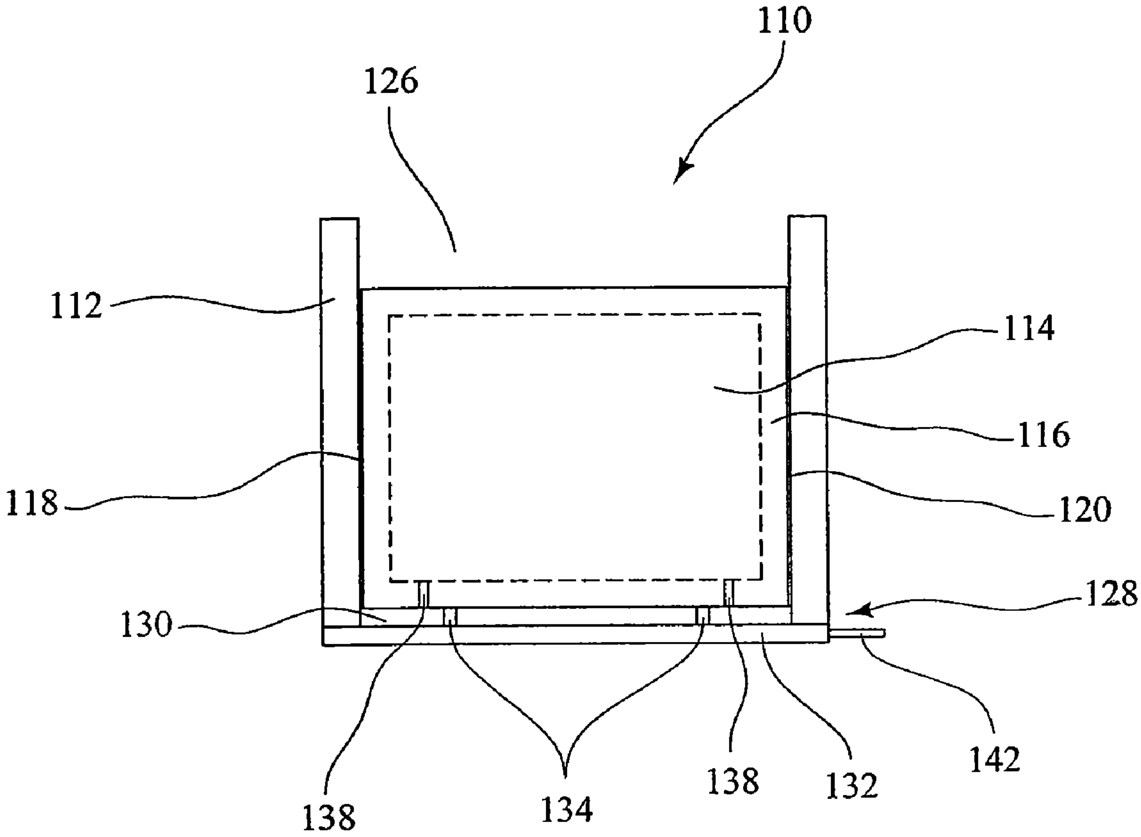
FIG. 9 is a cross-sectional view of a soap bar of the present invention in a mold having a second plate, which can be moved into place to close the drain holes of the mold.

Apparatus for coating and stripping of the core 12 is illustrated by FIGS. 5-9. in which a mold 112 is provided having four sides 118, 120, 122, 124, an open top 126, and a double plate bottom 128. The mold 112 comprises a material capable of withstanding the temperatures of the stripping and recharging process. The double plate bottom 128 of the mold 112 further comprises a first drain plate 130 in which are formed one or more drain openings 134 and a second plate 132 without any openings. The second plate 132 is moved relative to the drain plate 130 to open and close off the openings 134. In the embodiment shown in FIGS. 6-7, the second plate 132 is manually positioned inside the mold 112 to sit flush on the upper surface of the first plate 130, thereby closing the openings 134 while replenishing the soap layer 14 over the core 12. Alternatively, as shown in FIG. 9, the second plate 132 positioned outside of the mold 112 on the underside of the first plate 130 and linked to an arm 142 that is mechanically or manually pulled into position to close the openings 134 at the initiation of the recharging cycle.

Figure 5:
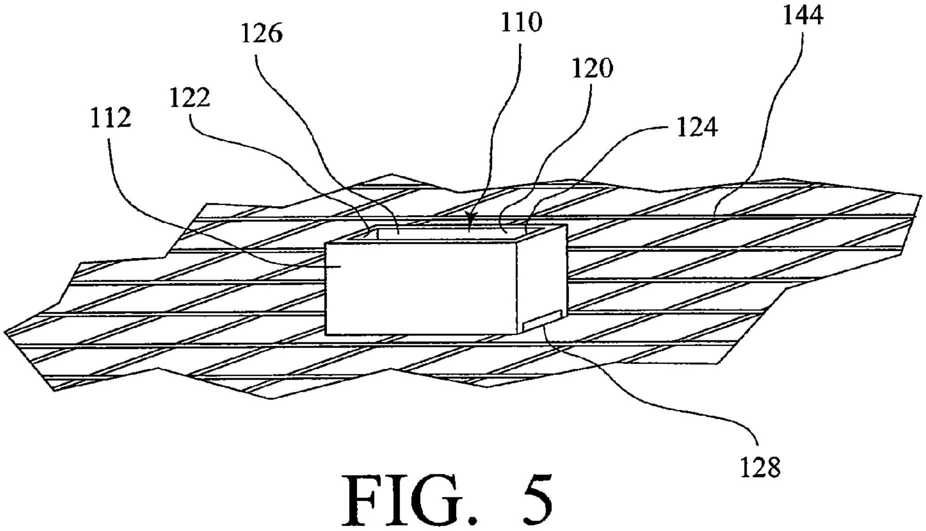
FIG. 5 is a perspective view of a soap bars of the present invention in an individual mold on a porous tray for stripping and recharging.
Figure 6:
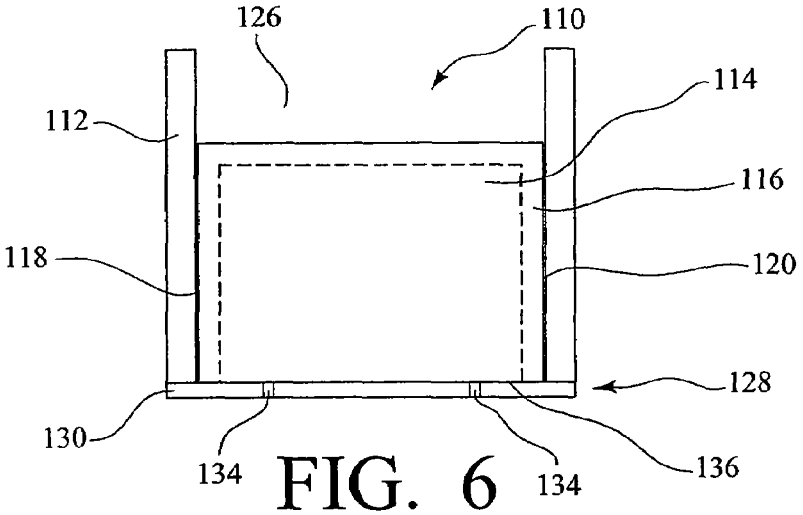
FIG. 6 is a cross-sectional view of a soap bar of the present invention in a mold for stripping and recharging in an open position.

In the embodiment shown in FIGS. 5-7, the core 114 is placed directly in the mold 112, touching the lower surface of the mold 112 at an interface 136 with the first plate 130 or second plate 132. However, it is conceived, and shown in FIG. 8, that the core 114 could be on at least one riser 138 to allow soap layer 140 to form on all sides of the core 114. The risers, as shown in FIG. 8, can produce an imprint, such as the name of the hotel, in a surface of the finished soap bar. It is within the scope of the invention to coat the core 12 in several steps. In this fashion the soap layers 14 can be of different colors or can be of a different type. Coating the core 12 in successive steps is particularly useful where it is desired to have indicia imprinted on the bar of soap.

Stripping and recharging a core 114, i.e. reapplying a fresh soap layer as described hereinafter proceeds through several cycles for used soap bars 110. However, it will be understood that in the case of applying a layer of soap over the core for the first time that the stripping cycle can be eliminated. The process described hereinafter is directed towards the stripping and replenishing a number of bars of soap simultaneously. However, it will be understood that the process will apply to the stripping and replenishment of bars of soap individually as well.

Referring to FIG. 5, the individual molds 112 are placed in a larger porous tray 144, that has one or more receptacles to hold the molds 112. For example, the large tray 136 as shown comprises an open top container where the molds 112 are adjacently placed. Alternatively, the large tray 144 may include defined receptacles for each mold 112. The large tray 144 is loaded into an apparatus adapted to spray water at hot temperatures and at sufficient pressure to strip any remaining soap layer from the core 12. As mentioned above suitable apparatus for stripping the core 114 is available such as for example, a commercial dishwasher that can be readily modified for application of the soap layer 116 over the core. Normally there are three cycles to the stripping and recharging process, with an alternate fourth cycle.

The first cycle is the "rinse" cycle, which strips residue of the soap layer 116 by a wash of hot water. When the first cycle is engaged, the plate 132 of the double plate 128 of the bottom of the mold is in an open position so that the openings 134 of the plate 130 are open for draining the mold. While the hot water strips the soap layer 116, drainage is directed through the openings 134 of the double plate 128 and washed out of the apparatus.

The second cycle is the soap layer application cycle. At the initiation of the second cycle, the double tray 128 is put into a closed position by positioning the plate 132 in relation to the drain plate 130 to close its openings 134. A soap composition, in a liquid phase, is introduced into the individual molds 12, such as from an overhead spray system (not shown). The overhead spray system can comprise a manifold or a series of tubes with appropriate spray nozzles directed to each mold 112. The soap composition is sprayed until the structural core 114 is fully covered within the mold or, as mentioned above, spraying may be carried out in several steps.

The third cycle is the cooling cycle. Cooling can be accomplished in the apparatus by simply allowing the soap layer to harden in the mold. The cycle can be accelerated, however, by the introduction a stream of cool air or by removing the large tray 144 containing the molds to an external chiller or by allowing the tray to sit at room temperature. The cooling process is complete when the soap layer 116 surrounding the structural core 114 is in a solid phase.

Although not critical to the process, a drying cycle can be inserted between the first and second cycles. During the drying cycle, the double plates 128 are in an open position and any further drainage is directed through the drains of the double plate 128 and out of the apparatus.

The soap layer surrounding the core can be any soap composition which is in a solid phase at room temperature, including but not limited to, hand soap, bath soap, transparent and nontransparent soap, glycerin soap and perfumed soap. Also, it is conceived that this could be used for lotions, including hand, body and suntan lotion. To keep the soap in a fluid condition prior to its application over a core 12, a coil is advantageously positioned around the soap container and the hot water used during the stripping operation can be circulated through the coil to maintain the soap in a fluid condition. Since the soap is fluid at a temperature of about 80-145 degrees F., the hot water used to strip the core provides sufficient heat energy to maintain the soap in a fluid state.

Alternatively, the cores 12 can be repeatedly dipped in liquid soap to form the soap layer 14 to complete the bar 10. This dipping procedure can provide a bar 10 of layered colors, or alternately, different types of soap, e.g. a cleanings soap alternating with a conditioning soap. The replenishing of the structural core 12 with the soap layer 14 of the present invention is what makes the structural core 12 a reusable soap bar 10.

Use of the soap bar 10 of the present invention allows an individual bar 10 to be placed in the hotel rooms, picked up each day, recharged and reused in the same or different hotel rooms. The recharging process produces a hygienic bar 10 ready for reuse.

It will be obvious to those skilled in the art that further modifications may be made to the embodiments described herein without departing from the spirit and scope of the present invention.

What is claimed is:

1. A method for recharging a soap bar comprising a structural core over one or more surfaces of which is deposited a solid layer of soap, said method comprising the steps of:

contacting the soap bar with a stripping fluid at a temperature above a softening point of said soap and at sufficient pressure to cause any existing soap layer to be stripped from any surfaces of said structural core;

placing said structural core in a pool of soap composition in a liquid phase and covering at least one surface of said structural core with said soap composition; and cooling said soap composition to form the solid layer of said soap over said at least one surface of said structural core.

2. The method of claim 1, wherein said structural core is comprised of material inert to said soap and said stripping fluid.

3. The method of claim 1, wherein said stripping fluid is water.

4. The method of claim 1, wherein said structural core comprises 25% to 90% of a volume of the soap bar.

5. The method of claim 1, wherein said structural core is a polymeric material selected from the group consisting of polyethylene, polyvinyl, polyurethane, polyolefin and combinations thereof.

6. The method of claim 1, wherein said structural core is placed inside a mold defining a cavity, and said cavity is filled with the soap composition in the liquid phase around said structural core.

7. A method for recharging a soap bar comprising a structural core over one or more surfaces of which is deposited a solid layer of soap, said method comprising the steps of:

placing said structural core in a mold having side walls and a bottom wall defining a desired shape for said soap bar;

stripping any existing soap layer from said structural core by a wash of liquid at sufficient temperature and pressure to strip said existing soap layer from any surfaces of said structural core;

transferring a soap composition in a liquid phase into said mold to cover at least one surface of said structural core;

cooling said soap composition to a solid phase; and removing said soap bar from said mold.

8. The method of claim 7, wherein said mold is contained in a tray having a porous lower surface during said stripping and transferring steps.

9. The method of claim 7, wherein said mold further defines a lower surface comprising a first plate and a second plate, said first plate having openings that are closed by said second plate underlying said first plate, and which are opened by moving said second plate away from said first plate thereby to provide fluid communication through said first plate.

10. The method of claim 7, wherein said structural core rests on risers during said stripping and transferring steps.

11. The method of claim 7, wherein said soap composition in the liquid phase is transferred into said mold by an overhead spray system.

12. A method for using a rechargeable soap bar comprising a structural core over one or more surfaces of which is deposited a solid layer of soap, said method comprising the steps of:

stripping any existing layer of said soap from any surfaces of said structural core;

depositing a soap composition in a liquid phase to cover at least one surface of said structural core;

cooling said soap composition to a solid phase; and after use, recovering said soap bar and repeating said stripping and depositing steps.

* * * * *